United States Patent [19]

Samson et al.

[11] Patent Number: 4,616,653
[45] Date of Patent: Oct. 14, 1986

[54] BALLOON DILATATION CATHETER WITH ADVANCEABLE NON-REMOVABLE GUIDE WIRE

[75] Inventors: Wilfred J. Samson, Saratoga; Jeffrey S. Frisbie, San Jose, both of Calif.

[73] Assignee: Advanced Cardiovascular Systems, Inc., Mountain View, Calif.

[21] Appl. No.: 760,397

[22] Filed: Jul. 30, 1985

[51] Int. Cl.⁴ .............................................. A61M 25/00
[52] U.S. Cl. ....................................... 128/344; 604/95; 604/170; 128/657; 128/348.1
[58] Field of Search ................................. 128/656–658, 128/772, 344, 348.1; 604/95, 170, 280, 96–103

[56] References Cited

U.S. PATENT DOCUMENTS

| | | | |
|---|---|---|---|
| 2,856,934 | 10/1958 | Petillo | 604/170 |
| 4,194,513 | 3/1980 | Rhine et al. | 604/256 X |
| 4,538,622 | 9/1985 | Samson et al. | 128/657 X |
| 4,545,390 | 10/1985 | Leary | 604/95 X |

Primary Examiner—Dalton L. Truluck
Attorney, Agent, or Firm—Flehr, Hohbach, Test, Albritton & Herbert

[57] ABSTRACT

Balloon dilatation catheter with an advanceable non-removable guide wire having a flexible tubular member with first and second lumens extending therethrough. An inflatable balloon is carried by the distal extremity of the tubular member so that the first lumen extends through the balloon and is out of communication with the interior of the balloon and in which the second lumen is in communication with the interior of the balloon. A guide wire is slidably mounted in the first lumen. A coil-like tip is secured to the distal portion of the guide wire and has a cross-sectional area which is greater than that of the cross-sectional area of the first lumen and prevents removal of the guide wire through the first lumen. The guide wire is capable of being advanced longitudinally of the first lumen so that the coil-like tip of the guide wire can be advanced ahead of the balloon to facilitate the positioning of the balloon.

7 Claims, 2 Drawing Figures

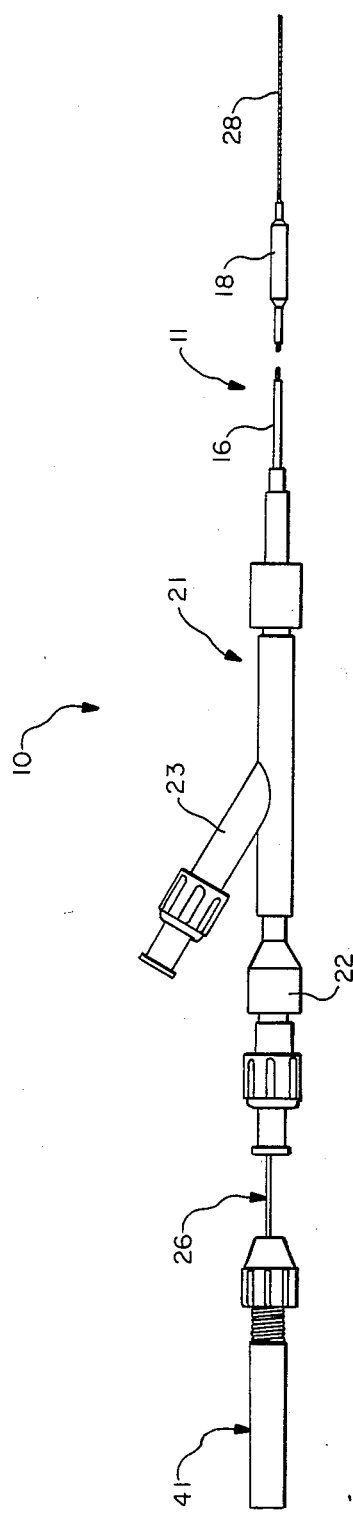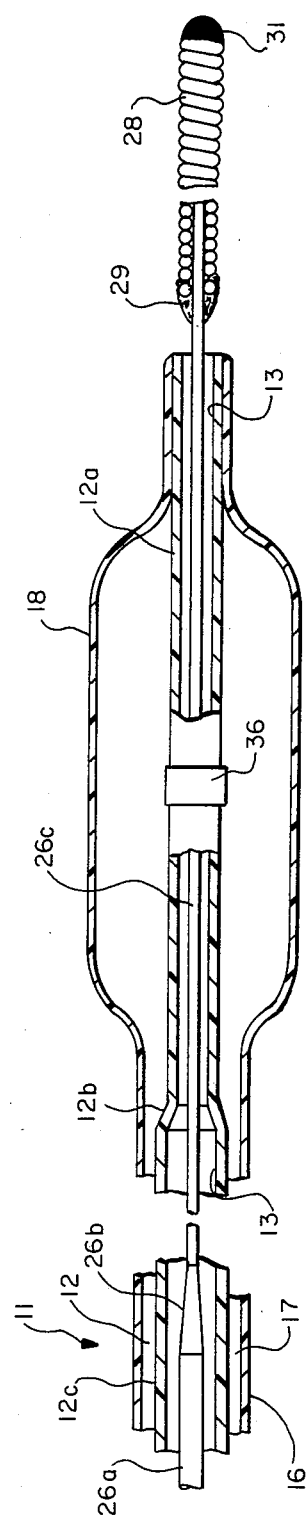

4,616,653

BALLOON DILATATION CATHETER WITH ADVANCEABLE NON-REMOVABLE GUIDE WIRE

This invention relates to a balloon dilatation catheter with an advanceable non-removable guide wire and more particularly to a balloon dilatation catheter of this type which has a very small collapsed balloon profile.

The size of the collapsed balloon profile in balloon dilatation catheters makes it possible to assess the potential ability of the balloon catheter to cross a lesion or stenosis. In general, the smaller the profile of the collapsed balloon, the tighter the lesion (or smaller the hole) the dilatation catheter will pass through. Consequently between two dilatation catheters having the same nominal inflated balloon diameters, the one with the smaller collapsed profile conceivably can cross tighter lesions and thus has a distinct advantage over one with a larger collapsed balloon profile. In balloon dilatation catheters using removable guide wires, the collapsed balloon profile has been reduced by reducing the outside diameter and the inside diameter of the guide wire lumen. This permits the balloon when evacuated and folded around the lumen to have a smaller effective diameter or, in other words, a smaller collapsed balloon profile. However, there is a limitation as to how much reduction in diameter can be obtained with such an approach because it is still necessary to be able to insert and remove the guide wire with such a balloon dilatation catheter. There is therefore a need for a new and improved balloon dilatation catheter with a guide wire in which it is possible to obtain still smaller collapsed balloon profiles.

In general it is an object of the present invention to provide a balloon dilatation catheter with an advanceable non-removable guide wire which has a small collapsed balloon profile.

Another object of the invention is to provide a catheter of the above character in which the guide wire is an integral part of the catheter.

Another object of the invention is to provide a dilatation catheter of the above character in which limited travel for the guide wire is provided.

Another object of the invention is to provide a catheter of the above character in which the guide wire can be advanced ahead of the balloon dilatation catheter to a limited extent.

Another object of the invention is to provide a balloon dilatation catheter of the above character in which the guide wire can be rotated.

Additional objects and features of the invention will appear from the following description in which the preferred embodiments are set forth in detail in conjunction with the accompanying drawings.

FIG. 1 is a side elevational view of a balloon dilatation catheter incorporating the present invention.

FIG. 2 is an enlarged cross sectional view of a portion of the balloon dilatation catheter shown in FIG. 1 and in particular shows the construction of the balloon.

In general, the balloon dilatation catheter with an advanceable non-removable guide wire is comprised of a flexible tubular element having first and second lumens extending therethrough. An inflatable balloon is carried by the distal extremity of the tubular member so that the first lumen extends through the balloon and is not in communication with the interior of the balloon and in which the second lumen is in communication with the interior of the balloon. A guide wire is slidably mounted in the first lumen. A coil-like tip is secured to the distal portion of the guide wire and has a cross-sectional area which is greater than that of the cross-sectional area of the first lumen which prevents removal of the guide wire through the first lumen. The guide wire is capable of being advanced longitudinally of the first lumen so that the coil-like tip of the guide wire can be advanced ahead of the balloon to facilitate the positioning of the balloon.

More particularly, as shown in FIGS. 1 and 2 of the drawing, the balloon dilatation catheter 10 incorporating the present invention consists of a flexible elongate tubular element 11 which is comprised of a first elongate flexible tubular element 12 which is provided with a first lumen 13 extending therethrough. The distal extremity of the tubular element 12 is provided with a portion 12a of reduced diameter with a transition region 12b which adjoins a portion 12c of a larger diameter and extending to the proximal extremity of the first tubular element.

A second elongate flexible tubular element 16 is also provided which extends over the first elongate tubular element 12 and is disposed coaxially therewith. The second elongate tubular element 16 is of a size so that there is provided between the first and second tubular elements 12 and 16 an annular lumen 17 extending the length of the tubular elements 12 and 16. A balloon 18 is carried by the tubular element 16 near the distal extremity thereof and has its interior in communication with the lumen 17. As shown, the balloon 17 is formed integral with the second tubular element 16.

The first and second tubular elements 12 and 16 can be formed of a suitable flexible thermo-plastic material such as a polyolefin or polyvinylchloride.

The distal extremity of the second elongate tubular element 16 is shrunk onto the distal extremity of the first tubular element 12 to form a liquid-tight seal between the distal ends of the same. With the construction shown it can be seen that the lumen 17 opens into the balloon 18 and can be used for inflating and deflating the balloon. It should be appreciated, if desired, instead of forming the balloon 18 integral with the second elongate tubular element 16 it can be formed as a separate element and bonded to the second tubular element by suitable means such as an adhesive.

An adapter 21 is secured to the proximal extremities of the tubular member 11 comprised of the first and second tubular elements 12 and 16. The adapter 21 is of a conventional type and is provided with a main or central arm 22 and a side arm 23. The main arm 22 is in communication with the lumen 13 of the first tubular element 12 and is adapted to carry a guide wire 26. The guide wire 26 can be formed of a suitable material such as stainless steel and is provided with an elongate portion 26a, a necked down portion 26b and a portion 26c at the distal extremity which is of substantially reduced diameter. A spring-like coil 28 is secured to the distal extremity of the guide wire 26 and as shown is in the form of a helix. The proximal end of the coil 28 is secured to the distal portion of the guide wire by suitable means such as solder 29. A semi-spherical tip 31 is provided at the distal extremity of the coil 28 and joins the tip of the wire to the coil. The coil 28 is formed of a suitable material such as platinum. The tip 31 can be formed of a suitable material such as gold.

A band 36 which serves as a marker is provided on the portion 12a of the first tubular element and is disposed substantially equidistant the extremities of the balloon 18.

A torquer 41 of a conventional type is secured to the proximal extremity of the guide wire 26 and is adapted to be grasped by hand for rotating the guide wire as hereinafter described.

If it is assumed that the balloon 18 has a diameter of two millimeters when fully inflated, the balloon dilatation catheter shown in FIGS. 1 and 2 of the drawings can have dimensions such as the following. The dilatation catheter 11 extending from the adapter 21 to the balloon 18 can have a suitable length ranging from 40 to 150 centimeters and preferably a dimension of approximately 135 centimeters. The first or inner tubular element 12 can have a portion 12c having an outside diameter ranging from 0.025 to 0.034 inches, an inside diameter of 0.014 to 0.020 inches and preferably 0.027 and 0.016 inches respectively. The portion 12a can have an outside diameter of 0.016–0.022 and an inside diameter of 0.008–0.012 and preferably dimensions of 0.020 for an outside diameter and 0.010 for an inside diameter. The second tubular element 16 can have an outside diameter of 0.038–0.048 and an inside diameter of 0.033–0.042 and preferably an outside diameter of 0.045 and an inside diameter of 0.038 inches. The balloon 18 can have a collapsed profile for a two millimeter balloon of 0.030–0.038 inches and can have a suitable length as, for example, 15 to 35 millimeters and preferably a length of approximately 25 millimeters. The distal extremity of the catheter in which the distal extremities of the first and second tubular elements are bonded together can have a suitable tip dimension ranging from 0.024–0.030 inches and preferably a dimension of 0.026 inches. This tip can have a length ranging from 3 to 10 millimeters and preferably a length of approximately 5 millimeters. The guide wire 26 can have its portion 26a with a dimension ranging from 0.013–0.014 inches and if desired can be coated with a suitable material such as Teflon. The portion of 26c of the guide wire 26 can have a dimension such as 0.007–0.008 inches. The coil 28 can have an outside diameter of 0.012 to 0.016 inches and preferably of approximately 0.015 inches. The coil 28 can have a length ranging from 1.5 centimeters to 5 centimeters and preferably has a length of approximately 3 centimeters. The radiopaque marker 36 can have an ID of 0.021 inches with a wall thickness of 0.002 and a width of approximately 0.045 inches.

Operation and use of the balloon dilatation catheter as shown in FIGS. 1 and 2 may now be briefly described as follows. Let it be assumed that it is desired to cross a stenosis which can only be entered with a dilatation catheter having a relatively small diameter. For such an application, the dilatation catheter 10 of the present invention having a relatively small balloon as, for example, the two millimeter balloon hereinbefore described can be utilized. The catheter 10 with the balloon 18 in a collapsed state is introduced into the vessel in a conventional manner. The guide wire 26 can be utilized to facilitate the introduction and advancement of the dilatation catheter 10. Its progress can be observed upon a fluoroscope because the coil 28 is relatively opaque to X-rays. Although the guide wire cannot be retracted from the catheter it is independently manipulable with respect to the balloon dilatation catheter. For example, if desired the distal extremity of the guide wire and, in particular, the coil 28 can be advanced so it is 3 or 4 inches ahead of the catheter. It also can be rotated by use of the torquer 41.

By utilizing such a guide wire with the dilatation catheter herein described, it is possible to reduce the profile of the dilatation catheter substantially with the only disadvantage being that the guide wire cannot be removed. The amount of travel of the guide wire is determined by the length of the portion 26c of the guide wire. When the tapered portion 26b enters the tapered portion 12b of the first tubular element, further travel is inhibited. The rearmost extremity of the guide wire is determined when the solder 29 reaches the distal extremity of the first flexible tubular element 12. Typically this extendability or advanceability of the guide wire in the dilatation catheter can vary from 10 to 20 centimeters. The amount of advancement of the guide wire 26 can also be adjusted within the limits just described by the positioning of the torquer 41 on the guide wire.

After the dilatation catheter has been positioned in the stenosis, the balloon 18 can be inflated by introducing a radiopaque contrast liquid through the side arm 23. The marker 36 provided within the balloon facilitates the positioning of the balloon in the stenosis prior to inflation. After the balloon has been inflated one or more times, the balloon can be deflated and the balloon removed from the stenosis and the dilatation catheter removed from the vessel.

It is apparent from the foregoing that there has been provided a new and improved balloon dilatation catheter which has a very small profile which is provided with a non-removable but advanceable guide wire to facilitate positioning of the balloon dilatation catheter. The balloon dilatation catheter is constructed in such a manner so that it can be readily fabricated to the desired tolerances.

What is claimed is:

1. In a balloon dilatation catheter with an advanceable non-removable guide wire, a flexible tubular member having first and second lumens extending therethrough, an inflatable balloon carried by the distal extremity of the tubular member so that the first lumen extends through the balloon and is out of communication with the interior of the balloon and in which the second lumen is in communication with the interior of the balloon and a guide wire slidably mounted in the first lumen, a coil-like tip secured to the distal portion of the guide wire and having a cross-sectional area which is greater than that of the cross-sectional area of the first lumen and preventing removal of the guide wire through the first lumen, said guide wire being capable of being advanced longitudinally of the first lumen so that the coil-like tip of the guide wire can be advanced ahead of the balloon to facilitate the positioning of the balloon.

2. A dilatation catheter as in claim 1 together with means secured to the guide wire to facilitate rotation of the guide wire in the first lumen.

3. A dilatation catheter as in claim 1 wherein said tubular member is comprised of a first tubular element having the first lumen extending therethrough, a second tubular element coaxially disposed over said first tubular element and forming the second lumen extending between the first and second tubular members and wherein the expandable balloon is carried by the second tubular element and has its interior in communication with the second lumen extending between the first and second tubular elements.

4. In a balloon dilatation catheter with an advancable non-removable guide wire, a first tubular element having a lumen extending therethrough, a second tubular element extending co-axially over the first flexible tubular element and forming a lumen between the first and second tubular elements extending longitudinally of the first and second tubular elements, an inflatable balloon carried by the distal extremity of the second tubular element and being in communication with the lumen formed between the first and second tubular elements, and a guide wire slidably mounted in the lumen in the first tubular element, a coil-like tip secured to the distal extremity of the guide wire and having a cross sectional area which is greater than that of the cross-sectional area of the lumen in the first tubular element and preventing removal of the guide wire through the lumen of the first tubular element, said guide wire being capable of being advanced longitudinally of the lumen in the first tubular element so that the coil-like tip of the guide wire can be advanced ahead of the balloon to facilitate the positioning of the balloon in a stenosis.

5. A dilatation catheter as in claim 4 together with means secured to the guide wire to facilitate rotation of the guide wire in the lumen of the first tubular element.

6. A dilatation catheter as in claim 4 wherein the portion of the first tubular element disposed within the balloon has a cross sectional area which is substantially less than the cross sectional area of the proximal portion of the first tubular element.

7. A dilatation catheter as in claim 6 wherein the guide wire extending through the lumen in the vicinity of the balloon has a cross-sectional area which is substantially less than the proximal extremity of the guide wire.

* * * * *